United States Patent [19]
Childress

[11] Patent Number: 4,865,814
[45] Date of Patent: Sep. 12, 1989

[54] AUTOMATIC STERILIZER
[75] Inventor: Bobby B. Childress, Charlotte, N.C.
[73] Assignee: Pelton & Crane, Charlotte, N.C.
[21] Appl. No.: 50,584
[22] Filed: May 15, 1987
[51] Int. Cl.[4] ............................................. G05B 19/00
[52] U.S. Cl. .............................. 422/116; 364/474.16;
364/551.01; 364/557; 364/558; 422/26;
422/108; 422/109
[58] Field of Search ...................... 422/3, 26, 108, 109,
422/110, 112, 116, 2, 62, 299; 364/551.01,
474.16, 556–558

[56] References Cited
U.S. PATENT DOCUMENTS

| | | | |
|---|---|---|---|
| 4,003,703 | 1/1977 | Montgomery, Jr. et al. | 422/116 X |
| 4,261,950 | 4/1981 | Bainbridge et al. | 422/26 |
| 4,309,381 | 1/1982 | Chamberlain et al. | 422/3 |
| 4,372,916 | 2/1983 | Chamberlain et al. | 422/26 |
| 4,447,399 | 5/1984 | Runnells et al. | 422/109 X |
| 4,710,350 | 12/1987 | Petersen | 422/109 X |

FOREIGN PATENT DOCUMENTS 0015328  2/1983  European Pat. Off.
3409365 10/1986  Fed. Rep. of Germany.
2052800  1/1981  United Kingdom.

Primary Examiner—Michael S. Marcus
Assistant Examiner—Amalia L. Santiago
Attorney, Agent, or Firm—Lawrence C. Edelman

[57] ABSTRACT

A microprocessor controls a heater which generates steam inside the sealed chamber of a sterilizer. During that portion of the sterilizer cycle wherein sterilizing conditions are trying to be attained, the microprocessor monitors both the temperature and pressure levels inside the chamber by controlling the heater and waits until both variables reach predetermined levels before starting a sterilize timer. Once the timer is started, it is stopped if the level of either one of the temperature or pressure variables drops below a predetermined minimum value which, in the preferred embodiment, air their optimum values. While the sterilize timer is timing, the pressure level rather than the temperature level is used by the microprocessor to control the heater. These features allow a more reliable and accurate control of the generation and maintenance of sterilizing conditions inside the chamber, resulting in greater assurance of complete sterilization while minimizing the expenditure of time and energy.

2 Claims, 3 Drawing Sheets

AUTOMATIC STERILIZER

BACKGROUND OF THE INVENTION

1. Field of the Invention

This invention relates to sterilizers and, more particularly, to the automatic operation of a steam sterilizer.

2. Description of the Prior Art

Sterilization criteria for steam sterilizers are conventionally defined by subjecting items to be sterilized to a high quality steam (such as saturated steam) at a given temperature for a predetermined period of time. The items are placed in a sealed chamber which is then filled with saturated steam. Unfortunately, when the items are placed inside the chamber, air also enters the chamber. It has long been recognized that the removal of this air is one of the most critical portions of a sterilizing process, since the presence of air in the chamber prevents proper sterilization conditions, i.e., saturated steam at a given temperature, from being accurately monitored inside the chamber. Thus, it is important to remove air from the chamber in order to develop and accurately monitor the saturated steam conditions inside the chamber and, once developed, to accurately maintain these conditions throughout the duration of the sterilization time period.

It is known that the pressure and temperature variables of saturated steam are dependent variables when saturated steam is enclosed in a sealed chamber. However, this dependency is destroyed if the saturated steam condition is not completely maintained throughout the chamber.

In a known sterilizer of the type which generates steam inside of the chamber, the user/operator must visually inspect the pressure and temperature displays and then manually start a sterilization timer when the proper conditions are attained. However, once the timer is started, if either of the pressure or temperature variables change beyond the limits defining the required conditions for the sterilizing steam, the manually controlled timer continues to operate and it is possible that the items will not be properly sterilized at the end of the timed period.

It is desirable to develop apparatus which would automatically control the generation of steam inside the sterilization chamber so as to insure proper sterilization conditions at both the start and during the sterilization cycle.

SUMMARY OF THE INVENTION

In accordance with the general principles of the present invention a microprocessor controller controls a heater which generates steam inside the sealed chamber of a sterilizer. In accordance with a first aspect of the invention, during that portion of the sterilizer cycle wherein sterilizing conditions are trying to be attained, the microprocessor controller monitors both the temperature and pressure levels inside the chamber by controlling the heater and waits until both variables reach predetermined optimum levels before starting a sterilization timer. In accordance with a further aspect of the invention, once the timer is started, it is stopped if the level of either one of the temperature or pressure variables drops below a predetermined minimum value which, in the preferred embodiment, are their optimum values. In accordance with a still further aspect of the invention, while the sterilize timer is timing, the pressure level rather than the temperature level is used by the microprocessor controller to control the heater. Each of these aspects of the invention allow a more reliable and accurate control of the generation and maintenance of sterilizing conditions inside the chamber, resulting in a greater assurance of complete sterilization while minimizing the expenditure of time and energy. Even further aspects of the invention are described relating to advantageous control arrangements for facilitating a completely automatic operation of the sterilizer.

Other features and advantages of the invention will be apparent from the description of the preferred embodiments and from the claims. For a fuller understanding of the present invention, reference should now be made to the following detailed description of the preferred embodiments of the invention and the accompanying drawings.

DETAILED DESCRIPTION OF THE PREFERRED EMBODIMENT

Figure 1:
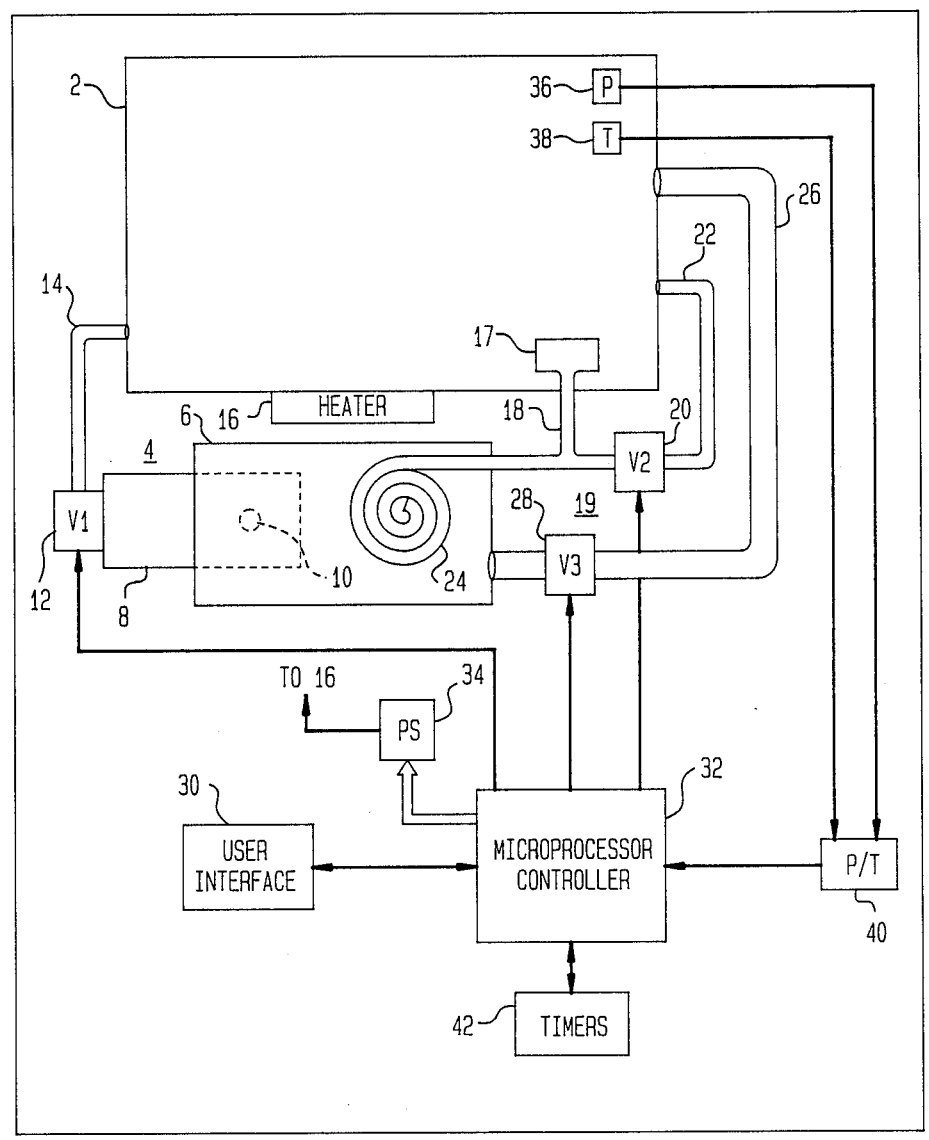
FIG. 1 illustrates in block diagram form a top view of the electrical and mechanical components of an automatic sterilizer of the present invention.

The mechanical portion of the sterilizer of FIG. 1 includes a sterilizing chamber 2 having a door (not shown) for allowing access for a user to place items inside of chamber 2 which are to be sterilized. A dosing arrangement 4 introduces a premeasured amount of liquid such as distilled water, into chamber 2. Dosing arrangement 4 includes a supply tank or reservoir 6 coupled to a dose tank 8 via a liquid flow path 10. The volume of dose tank 8 is substantially less than that of reservoir 6, and holds precisely that amount of water which is needed to produce the correct amount of steam inside chamber 2 for sterilization purposes. A solenoid controlled valve (V1)12 controls both the entrance of water into dose tank 8 and the flow of water from dose tank 8 into chamber 2 via an inlet line 14. Dosing arrangement 4 can be constructed in a variety of well known ways, e.g., as shown German Patent Publication No. 34 09 365. Alternatively, dosing arrangement 4 can comprise the arrangement shown in U.S. patent application Ser. No. 045,968, filed on May 1, 1987 and having the same assignee as in the present application. A heater 16 attached about the outside circumference of chamber 2 is used to heat the water (via heating of the chamber) to make the sterilizing steam, and after the sterilization cycle is completed, to heat the air inside of chamber 2 in order to dry the sterilized items. While steam is being generated inside chamber 2, a conventional air-bellows 17 coupled to chamber 2 vents the air which is being displaced from the chamber by the generated steam, as well as cool steam, into reservoir 6 via a flow path 18. As well known, a mixture of water and alcohol contained within bellows 17 is heated by the steam inside of chamber 2 and when the steam reaches the optimum value, causes the mixture to expand and thereby close the air-bellows vent. A further vent arrangement 19 is used to vent the steam from chamber 2 after the completion of the sterilization cycle. As is conventional in the prior art, vent arrangement 19 includes a solenoid operated valve (V2)20, for controlling the venting of steam, and any residual water, from chamber 2 into reservoir 6 via a flow path comprising an outlet line 22 and a condensing coil 24. Condensing coil 24 is located within reservoir 6 and slows the flow of the venting steam so as to allow it to be cooled by the water inside of reservoir 6 and return to a liquid phase. Flow path 18 for air-bellows 17 is also connected to the input of condensing coil 24. Once the chamber pressure reduces to a predetermined lower level, a more rapid exhaust is provided by a high flow rate exhaust (dump) line 26 connected between chamber 2 and reservoir 6, which is controlled by a solenoid operated valve (V3)28.

The electronic portion of the sterilizer includes a user interface 30 having control switches (not shown) for allowing a user to select a preprogrammed operating mode for the sterilizer, e.g., a preset time/temperature/pressure cycle for sterilizing a selected type and quantity of items placed inside of chamber 2. Additionally, user interface 30 includes pressure and temperature displays for indicating the temperature and pressure conditions inside of chamber 2 and a printer for providing a hard copy of the daily operation of the sterilizer. A microprocessor controller 32 is responsive to control signals from user interface 30 for operating valve 12 so as to control the flow of water into and out of dose tank 8, for operating valves 20 and 28 for controlling the venting of steam from chamber 2 and for controlling a power supply (PS) 34 which supplies power to heater 16. Power supply 34 is controlled by microprocessor controller 32 so as to cause heater 16 to generate the correct pressure and temperature of sterilizing steam during the cycle of the sterilization and heat during the drying cycle of the sterilizer. The pressure and temperature conditions inside of chamber 2 are sensed by pressure (P) and temperature (T) sensors 36 and 38, respectively, and a pressure/temperature module (P/T) 40 coupled to sensors 36 and 38, develops pressure and temperature representative signals which are provided to microprocessor controller 32. It should be understood that pressure and temperature sensors 36 and 38 may in fact comprise several sensors each and be placed in various positions with respect to chamber 2. For example, temperature sensor 38 may comprise a first sensor (not shown) positioned on the chamber wall to monitor its temperature and second sensor (not shown) positioned so as to monitor the steam temperature inside of chamber 2. As will be described later on, the first sensor is mainly used for controlling the standby and drying operation of the sterilizer and the second one is used for controlling the sterilizing operation. Microprocessor controller 32 also provides control signals to the display and printer portions (not shown) of user interface 30, in order to provide the user with indications concerning the operation of the sterilizer.

Although not shown, microprocessor controller 32 includes an A/D converter for digitizing the pressure and temperature signals supplied thereto from P/T module 40 and memories for storing preprogrammed and user programmed operating instructions. Although timers 42 are illustrated which are used for controlling the overall timing of the sterilizer cycles, such timing functions are generally carried out internal to the microprocessor controller. Furthermore, it should be noted that although the control signals for valves 12, 20 and 28 are illustrated as being supplied from microprocessor controller 32, due to power limitations inherent in the output signal of a microprocessor, in practice these signals would be supplied to valves 12, 20 and 28 from power supply 34 under control from microprocessor controller 32.

Figure 2A:
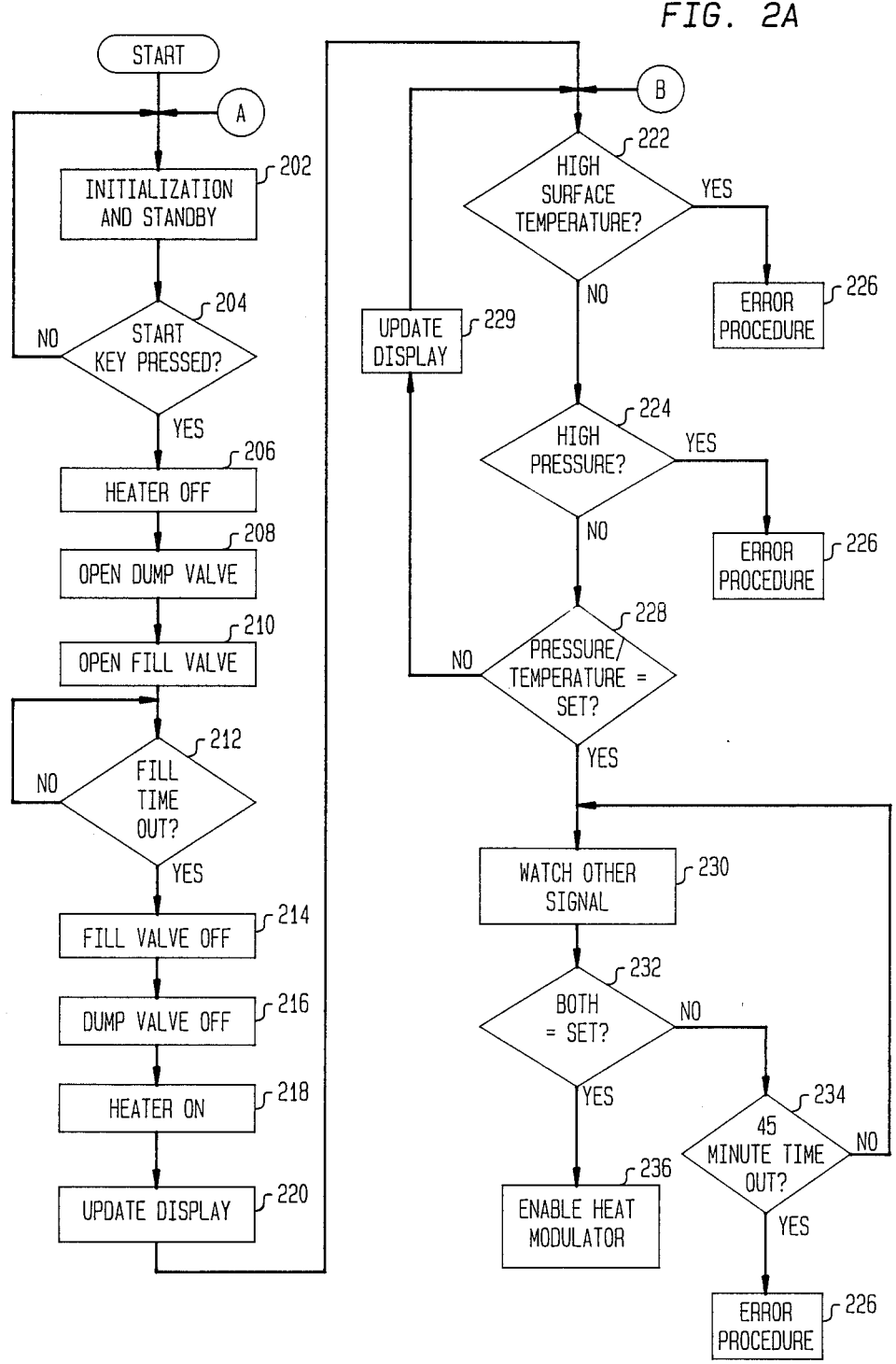
FIGS. 2a and 2b illustrate a flow chart of the operation of the sterilizer of FIG. 1.
Figure 2B:
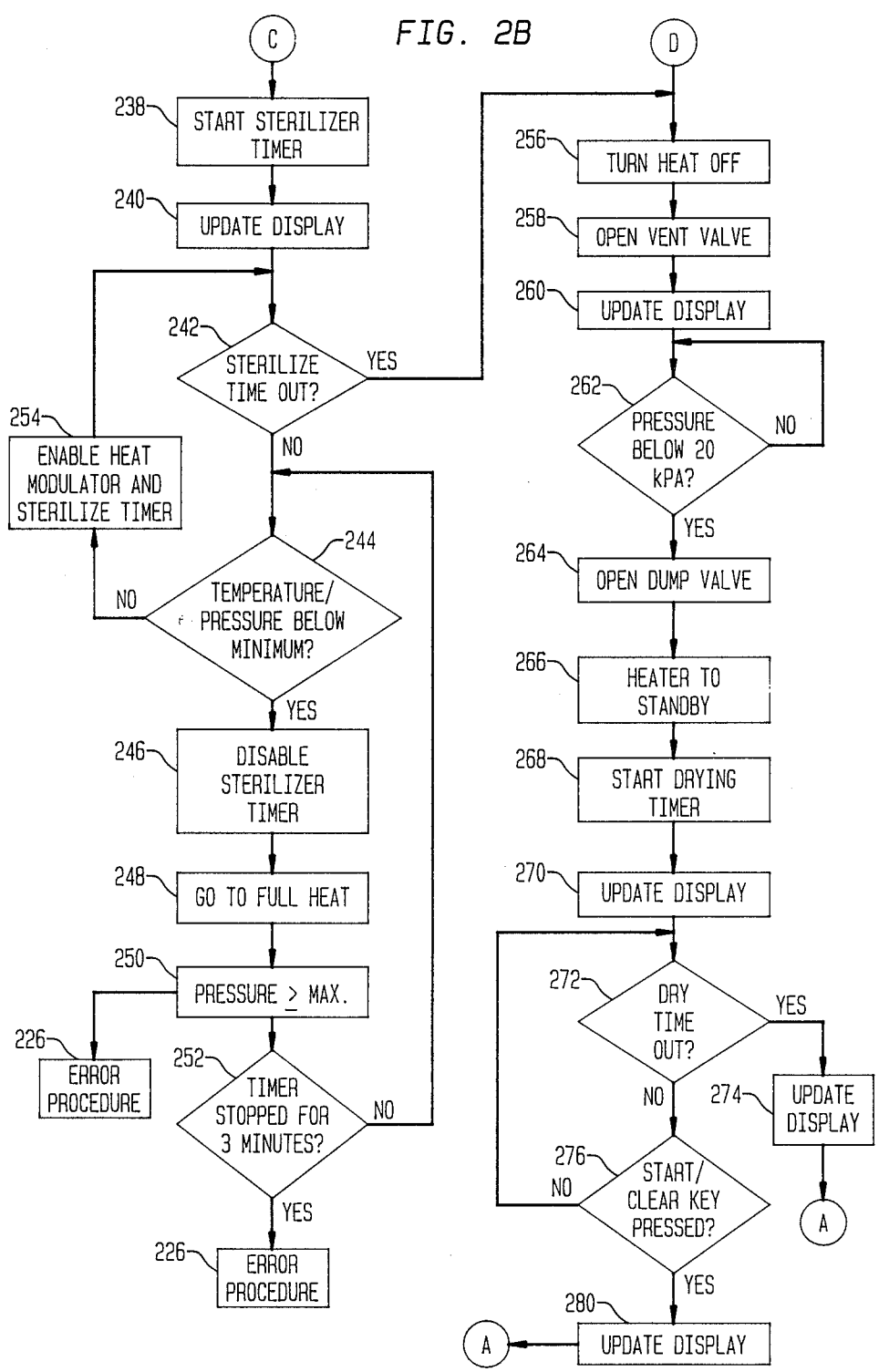

As will be described next in conjunction with the flow chart of FIGS. 2a and 2b, in accordance with a first aspect of the present invention, the sensed level of both the pressure and temperature conditions inside chamber 2 are required to reach predetermined optimum levels before microprocessor controller 32 begins timing the duration of the sterilization time period. In accordance with a second aspect of the invention, once the sterilization time period has been begun, the level of the pressure signal is used by microprocessor controller 32 to control heater 16, and in accordance with a still further aspect of the invention, microprocessor controller 32 stops timing the sterilization time period if the level of either one of the pressure or temperature signals falls below a predetermined minimum value.

The operation of the sterilizer will now be described with reference to the flow charts of FIGS. 2a and 2b. Block 202 represents an energized condition of the sterilizer wherein process initialization is performed and the sterilizer is placed in a standby (ready) mode. Initialization process includes user selection of the operating mode and/or selection of the sterilizing conditions, via user interface 30, as well as an internal diagnostic check by microprocessor controller 32 of the operability of various subsystems/components of the sterilizer. The standby mode basically comprises maintaining a portion of the base or wall of chamber 2 at a set minimum temperature (i.e., 140° C.) by selective application of a heat control signal to heater 16.

Block 204 represents interrogation of user interface 30 for determining if a start key has been depressed. If not depressed, the procedures of block 202 are repeated. If depressed, heater 16 is turned off by substantially reducing to zero the level of the heat control signal (e.g., removal of the heat control signal) and the dump and fill valves 28 and 12 are opened, as shown by blocks 206, 208 and 210. Dump valve 28 is opened during the fill cycle to prevent the build up of steam pressure when fill valve 12 is opened, since the chamber door is closed and chamber 2 is already hot from either a prior use or heating during the standby mode.

In prior art sterilizers, the chamber door had to be left open during the fill cycle in order to prevent this build up of pressure during the fill cycle which would disadvantageously slow the fill rate from the dose tank into the chamber. Although one would think that it would not be necessary in the present automatic sterilizer to turn off the heater at this point in the cycle (since the dump valve is open), it is in fact particularly advantageous to do so, in order to minimize the cost of the automatic sterilizer. This is true because if the heater was not turned off, the dump valve may not have a large enough diameter to handle the "flash" vapor generated when the cool water enters the hot chamber during filling. Although the dump valve could have a larger diameter, this would necessitate the use of a more powerful and therefore more expensive solenoid operator for the valve, undesirably increasing the cost of the sterilizer.

Block 212 represents a timer function provided by microprocessor controller 32 for controlling how long fill valve 12 remains open. Since there is no build up of pressure it can be safely assumed that dose tank 8 has completely drained into chamber 2 at the end of a relatively short time period, i.e., one minute, and thereafter, the fill and dump valves are closed, heater 16 is turned full on and the display of user interface 30 is updated to indicate the end of the fill cycle and thereafter the increasing temperature and pressure conditions inside chamber 2, as represented by blocks 214, 216, 218 and 220.

While air-bellows 17 allows the air to be expelled from chamber 2, the increasing chamber surface temperature and internal pressure levels are monitored by microprocessor controller 32, as indicated by blocks 222 and 224. If the surface temperature exceeds a preset maximum level, it is indicative of not enough water inside of chamber 2 for completing the sterilize cycle. If the pressure. inside of chamber 2 exceeds a preset maximum value, it indicates i.e., a defective air-bellows 17. If either of these conditions are met, microprocessor controller 32 goes into an error procedure which comprises: opening vent valve 20, updating the display to indicate the error, turning off heater 16 and going to the standby mode.

If there is no temperature or pressure caused error condition, microprocessor controller 32 monitors the steam temperature and pressure levels for determining if either one reaches its respective preset levels for sterilization, i.e., 132° C. at 210 kPa above atmospheric, as shown by block 228. If neither signal reaches its preset level, the display is updated to indicate the present pressure and temperature and the function of blocks 222-229 are repeated. When either one of the pressure or temperature signal levels reach its respective preset level, the other signal is then monitored until it reaches its preset level, as indicated by blocks 230, 232 and 234. If both signals don't reach their preset levels within a preset time period, i.e., 45 minutes from the end of the fill cycle, block 234 terminates the cycle by reverting to an error procedure, block 226. However, if both signals do reach their preset levels within the specified time period, a heat modulator is enabled, a sterilize timer is started and the display is updated to indicate the start of the sterilization cycle, as indicated by blocks 236, 238, and 240. The heat modulator is a function performed by microprocessor controller 32 which causes a heat signal with, i.e, a 0-100% duty cycle, to be applied to heater 16, for maintaining the preset pressure and temperature conditions inside of chamber 2 which are determinative of the sterilization condition. When the preset conditions are reached, a 50% duty cycle is generally supplied to the heater.

As shown by blocks 244, 246 and 248, if the sterilization timer has not timed out, microprocessor controller 32 determines if the pressure or temperature steam levels inside the chamber 2 have dropped below a minimum level, i.e., 131° C. and 207 kPa, which is slightly less than the preset levels required for optimum sterilization conditions (which optimum conditions are normally maintained by the heat modulator function of block 236). If these signal levels drop below the minimum level, the sterilization timer is stopped and a heat signal is directly applied to heater 16, thereby disabling the modulator function of block 236. As shown by block 252, if the sterilize timer is stopped for less than a predetermined period, i.e., 3 minutes, blocks 244-252 are repeated. If, however, 3 minutes has elapsed, this is indicative of a fault or other failure and an error procedure 226 is initiated. Furthermore, as shown by block 250, if during this 3 minute time period the pressure level exceeds a preset maximum level, also indicative of a fault or other abnormal condition, an error procedure 226 is also initiated. Additionally, as shown by block 244 and 254, if during this 3 minute period the pressure and temperature signal levels increase to the point where they exceed their minimum levels, the heat modulator function and sterilization timer are again enabled.

When the sterilization timer times out, the sterilization time period is over and there is assurance that the items placed inside chamber 2 have been properly sterilization. The venting of the pressure inside chamber 2 is indicated by blocks 256–264. Initially, heater 16 is turned off, vent valve 20 is opened and the display is updated to indicate the end of the sterilization cycle. Since during venting the pressure is lower than the preset pressure used during sterilization, the chamber temperature would disadvantageously increase during venting if heater 16 were not positively turned off at this point in the sterilizer operation. In order to speed up the venting process, once the pressure inside chamber 2 falls below 20 kPa, dump valve 28 is opened, as indicated by blocks 262 and 264. The dry cycle then begins, as indicated by blocks 266, 268 and 270, wherein microprocessor controller 32 returns the control of heater 16 to the standby mode (i.e., 140° C.), starts an internal timer for timing the dry cycle and updates the user interface display to indicate the sterilizer is in the dry cycle. As shown by blocks 272 and 274, when the dry time period ends, the display is updated to indicate the standby mode or, if the dry cycle is interrupted and the start or clear key is pressed, the display is also updated to indicate return to the standby mode, as indicated by blocks 276 and 280.

Thus, there has been shown and described novel apparatus for automatically controlling a sterilizer which fulfills all of the objects and advantages sought therefore. Many changes, modifications, variations and other uses and applications of the subject invention will, however, become apparent to those skilled in the art after considering this specification and the accompanying drawings, which disclose a preferred embodiment thereof. For example, it is not necessary that the liquid used by the sterilizer be distilled water and in fact may comprise some other liquid which is turned into a vapor phase by the heater. All such changes, modifications, variations and other uses and applications which do not depart from the spirit and scope of the invention are deemed to be covered by the invention which is only limited by the claims which follow.

I claim:

1. Sterilizing apparatus, comprising:
   a chamber for receiving items to be sterilized;
   means coupled to said chamber for sealing said chamber so as to be able to withstand an internal pressurization;
   dosing means coupled to said chamber for allowing the entry into said chamber of a predetermined amount of liquid in response to a DOSE control signal;
   a heater coupled to said chamber for heating the interior thereof in response to a HEAT control signal;
   pressure and temperature signal generating means for providing pressure and temperature signals, respectively, representative of pressure and temperature conditions, respectively, inside said chamber;
   a timer for timing the duration during which sterilizing conditions are maintained inside said chamber, said timer being started and stopped in response to START and STOP control signals, respectively; and a microprocessor controller for generating said DOSE, HEAT, START and STOP control signals and for causing said DOSE, HEAT, START and STOP control signals to be applied to said dosing means, heater and timer, respectively, (a) said microprocessor controller causing said DOSE and HEAT control signals to be applied at the beginning of a sterilization cycle of said sterilizer so as to generate a vapor phase of said liquid which is allowed to enter said chamber, and thereafter monitoring both said temperature and pressure signals until they both reach predetermined set levels and, when reaching said predetermined set levels, providing said START control signal to said timer;

(b) said microprocessor controller including monitor means for monitoring said pressure and temperature signal levels after said timer has been started and if the level of either of said signals falls below a predetermined minimum level, providing said STOP control signal to said timer so as to stop said timer; and (c) said microprocessor controller including additional timing means for timing a preset duration after said monitor means has provided said STOP control signal, and if both said pressure and temperature signal levels reach their said minimum levels before said preset duration ends, said monitor means restarts said timer and said microprocessor controller causes said HEAT control signal to be applied to said heater in response to the level of said pressure signal.

2. Sterilizing apparatus, comprising:

a chamber for receiving items to be sterilized;

means coupled to said chamber for sealing said chamber so as to be able to withstand an internal pressurization;

dosing means coupled to said chamber for allowing the entry into said chamber of a predetermined amount of liquid in response to a DOSE control signal;

a heater coupled to said chamber for heating the interior thereof in response to a HEAT control signal;

pressure and temperature signal generating means for providing pressure and temperature signals, respectively, representative of pressure and temperature conditions, respectively, inside said chamber;

a timer for timing the duration during which sterilizing conditions are maintained inside said chamber, said timer being started and stopped in response to START and STOP control signals, respectively; and a microprocessor controller for generating said DOSE, HEAT, START and STOP control signals and for causing said DOSE, HEAT START and STOP control signals to be applied to said dosing means, heater and timer, respectively, (a) said microprocessor controller causing said DOSE and HEAT control signals to be applied at the beginning of a sterilization cycle of said sterilizer so as to generate a vapor phase of said liquid which is allowed to enter said chamber, and thereafter monitoring both said temperature and pressure signals until they both reach predetermined set levels and, when reaching said predetermined set levels, providing said START control signal to said timer;

(b) said microprocessor controller including monitor means for monitoring said pressure and temperature signal levels after said timer has been started and if the level of either of said signals falls below a predetermined minimum level, providing said STOP control signal to said timer so as to stop said timer; and (c) said microprosser controller including additional timing means for timing a preset duration after said monitor means has provided said STOP control signal, and if both said pressure and temperature signal levels do not reach their said minimum levels by the end of said preset duration, said microprocessor controller removes said HEAT control signal from said heater and said sterilization cycle is terminated.

* * * * *